United States Patent
Butnaru

Patent Number: 5,966,680
Date of Patent: Oct. 12, 1999

[54] MOTION SICKNESS/VERTIGO PREVENTION DEVICE AND METHOD

[76] Inventor: Hanan Butnaru, 1 Somerville Ct., San Antonio, Tex. 78257

[21] Appl. No.: 08/800,266

[22] Filed: Feb. 13, 1997

Related U.S. Application Data

[60] Provisional application No. 60/011,895, Feb. 15, 1996, and provisional application No. 60/017,753, May 15, 1996.

[51] Int. Cl.$^6$ .................................................. B07C 1/20
[52] U.S. Cl. ........................................ 702/150; 175/40.44
[58] Field of Search ............................ 702/150; 359/14; 175/40.44

[56] References Cited

U.S. PATENT DOCUMENTS

| | | | |
|---|---|---|---|
| 5,051,735 | 9/1991 | Furukawa | 340/705 |
| 5,138,555 | 8/1992 | Albrecht | 364/424.06 |
| 5,613,022 | 3/1997 | Odhner et al. | 385/37 |
| 5,717,392 | 2/1998 | Eldridge | 340/996 |
| 5,727,098 | 3/1998 | Jacobson | 385/31 |
| 5,729,366 | 3/1998 | Yang | 359/13 |
| 5,745,054 | 4/1998 | Wilkens | 340/972 |

OTHER PUBLICATIONS

"Performance and Well–Being Under Tilting Conditions: The Effects of Visual Reference and Artificial Horizon" by A. Rolnick and W. Bles, Aviation Space Environmental Medicine, 60(8); 779–785, 1989 Aug.

"A Retinal Display for Virtual–Environment Applications" by Joel S. Kollin, 1993 International Symposium, Digest of Technical Papers, vol. XXIV (p. 827).

*Primary Examiner*—Marc S. Hoff
*Assistant Examiner*—Linh Nguyen
*Attorney, Agent, or Firm*—Jenkens & Gilchrist, P.C.

[57] ABSTRACT

A device and method which operates as an artificial labyrinth to eliminate sensory mismatch between the natural labyrinth/vestibular system and the vision system of an individual. The present invention provides an alternative means for the user to determine the true orientation of his body with respect to the surrounding environment. The method can be effected by means of a device which senses true body orientation and displays corresponding visual orientation cues that the brain can use to confirm other visual position information. The display can be projected into space in front of the user, directly onto the user's retina, or effected by pictorial scene averaging. The device is particularly useful in the rehabilitation treatment of persons suffering from vestibular nervous system defect or damage, and in providing relief to those suffering from the symptoms of nausea and/or vertigo which are often experienced as a result of the aforementioned sensory mismatch.

30 Claims, 9 Drawing Sheets

MOTION SICKNESS/VERTIGO PREVENTION DEVICE AND METHOD

This application claims the benefit of U.S. Provisional Application Nos. 60/011,895, filed on Feb. 15, 1996, and 60/017,753, filed on May 15, 1996.

BACKGROUND OF THE INVENTION

1. Field of the Invention

The present invention relates generally to a device for the relief of nausea, disorientation, and other disabling symptoms resulting from sensory mismatch and, more particularly, to an artificial labyrinth which provides the user an alternate means of determining his actual, physical orientation with respect to the surrounding environment.

2. Background of the Invention

Motion sickness does not discriminate. It can attack anyone, at any time. It is always disabling, to a greater or lesser degree, depending on the person. It is known from research that certain types of sensory mismatch are the leading cause of motion sickness. This mismatch occurs when the brain perceives that the body is in motion (through signals originating in the labyrinth and transmitted to the brain by the vestibular nerve system), but the motion sensed does not match what the eye can see and verify. The reverse is also true (i.e. sensory mismatch may also occur when the eye perceives motion, but the labyrinth does not provide confirming signals to the brain). There are many causes of this mismatch, including: time delay between the arrival of labyrinth motion signals and visual confirmation signals within the brain, or conflict between these signals when they do manage to arrive at the same time. In addition, the labyrinth's signals may be corrupted by various physical defects, conflict with each other within the labyrinth, or be missing entirely, as is the case when a person has the vestibular system disconnected (via operation, accident, or birth defect). All causes of this type of sensory mismatch are not precisely known, but it is well-established that such conditions can drastically affect an individual's quality of life and performance of everyday tasks.

One example of sensory mismatch is vertigo, which is the sensation the brain encounters when it perceives that the body is in motion (when in fact there is no motion), and it attempts to correct bodily posture to counteract the perceived physical sensation. Another example of sensory mismatch occurs when the eye perceives motion, but no motion actually occurs. This can be described as a type of "virtual reality" sickness, which is normally experienced users of video games or flight simulators. The reverse situation, when the body feels motion but there are no visual cues, is a much more common occurrence. Examples include: passengers in an airplane with no access to a window, sailors in a submarine, and ship passengers that cannot see the horizon. Such persons sense actual changes in body position, but have nothing in the environment which allows their eye to confirm the motion they perceive.

It is not clear why some persons can tolerate sensory mismatch better than others. However, at some point, almost everyone is affected when the mismatch is severe. This is especially true for those who, through accident or genetic deficiency, suffer from vestibular system disfunction. That is, even though the person is sitting or standing in a stationary fashion, they have the constant feeling of motion and, as a result, sickness. Simply bending over or slight movement of any kind may result in total disability in these cases. In the United States alone, over 30,000 vestibular section operations occur each year to help those suffering from Meniere's disease (i.e. vertigo induced by a distended labyrinth) get some relief, which drugs alone can't provide. However, rehabilitation after such an operation may require months of therapy.

Several attempts have been made to alleviate the symptoms of motion sickness (e.g., drugs which numb the nervous system and give some relief from nausea), but no successful product exists to eliminate the cause of motion sickness. Even if the resulting nausea is somewhat lessened, the sensory mismatch still exists, and may cause the affected person to make improper or dangerous decisions when accomplishing everyday tasks, such as driving an automobile.

Thus, there exists a long-felt and widespread need to provide alternative environmental orientation information (i.e. "visual cues") which can be used by the brain to replace erroneous or missing sensation signals normally provided by the natural labyrinth, and which can be readily confirmed by the natural vision system. The method and apparatus of the present invention, discussed in greater detail below, clearly satisfies this need.

SUMMARY OF THE INVENTION

The present invention provides an artificial labyrinth which augments or replaces the natural labyrinth. It functions by sending visual cue orientation information directly to the eye for transmission to the brain. After some training by the user, the brain will learn to compare the artificial labyrinth orientation cue information with the visual perception of the user, and to disregard misleading natural labyrinth signals.

The artificial labyrinth can exist in the form of a wearable accessory usable by any number of people; it can be integrated into glasses already worn for vision correction, or can be used with an independently wearable frame or other apparatus which enables a portable system to be devised. It is specifically designed to take advantage of miniature gyroscope, accelerometer, magnetostrictive sensor, or other attitudinal sensing technology to produce a device and method which give the user constant visual cues as to his orientation with respect to the surrounding environment. Such cues, when substituted by the brain for erroneous signals sent by a dysfunctional labyrinth or vestibular system, serve to eliminate sensory mismatch and the resulting sensations of nausea or vertigo.

Visual cues can be supplied in a number of ways, including: a series of lines projected into the space in front of the user by way of a display or projection mechanism such as the commercially-available "Private-Eye™"; direct projection of visual cues onto the retina; laser holography; or some type of averaged video display which records the image in front of the user, and re-displays a series of averaged video frames to the user's eye in order to give the appearance of a stable platform—much like the technology some commercial movie cameras use to stabilize an image while the camera is being moved during operation.

In the presently preferred embodiment, by way of example and not necessarily by way of limitation, the artificial labyrinth makes use of a triaxial accelerometerto produce visual cues indicating the user's actual pitch and roll motion. The accelerometer is mounted on the user's head and the resulting electrical output from each axis (which reflects movement) is sampled every 10 msec. After 12 sample cycles occur (120 msec), the accelerometer signal data is averaged for each axis, compared with the user's baseline position (i.e. at rest), and translated into visual cues for display. The visual display is updated several times a second (at least every 150 msec) so that reference orientation cues are timely delivered to the eye for transmission to the brain. It has been determined through experimentation that such feedback eliminates sensory mismatch between the labyrinth/vestibular system and the visual system, so as to give relief to many who suffer from vertigo or motion sickness.

The basic system can also be enhanced by the inclusion of magnetic sensors, which allow the addition of visual cues to indicate the yaw of the user. Thus, users can receive visual verification of rotational changes which occur to the left or right about a vertical axis which extends from the head to the toes. Elevational changes can likewise be communicated to the user by way of visual cues, as well as other useful, but non-orientation related (e.g. mapping or message) information.

The artificial labyrinth satisfies a long existing need for a system capable of quickly, accurately, and inexpensively eliminating the sensory mismatch which is induced by environmental conditions or labyrinth/vestibular system dysfunction. The above and other advantages of this invention will become apparent from the following more detailed description, in conjunction with the accompanying drawings and illustrative embodiments.

DETAILED DESCRIPTION OF THE PREFERRED EMBODIMENT

Figure 1:
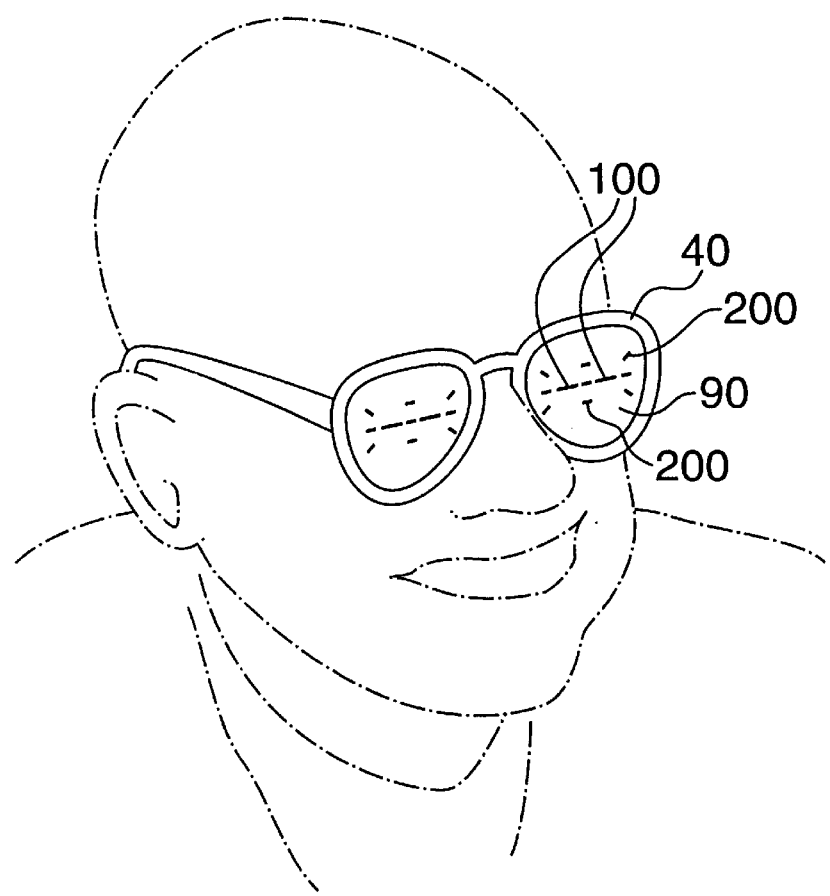
FIG. 1 is a perspective view of the present invention as worn by a user.

FIG. 1 illustrates a perspective view of one embodiment of the present invention, as it may be worn by a user. Glasses frames (40) encompass lenses (90), which provide a display to the user having fixed orientation marks (200) and movable visual cue orientation marks (100).

Figure 2:
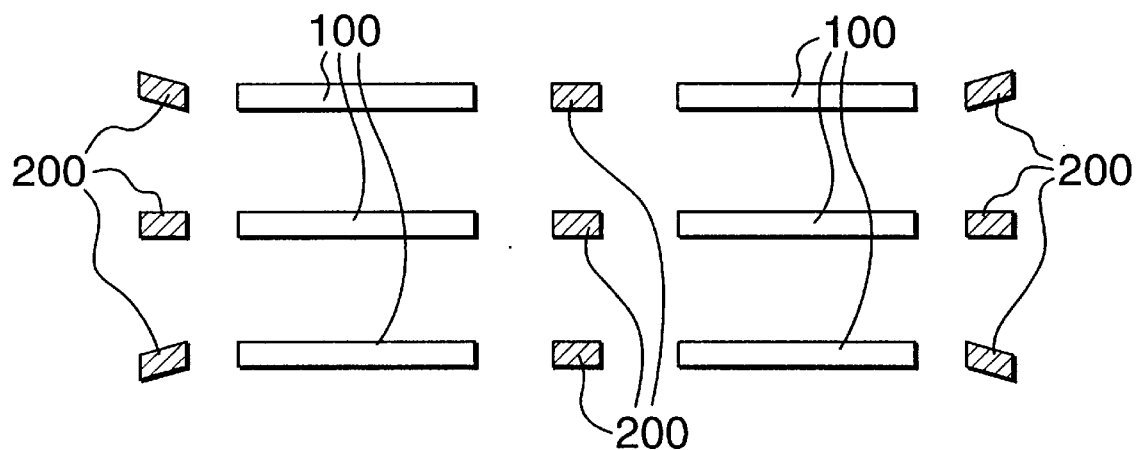
FIG. 2 is a stylized example of a visual cue display.
Figure 3A:
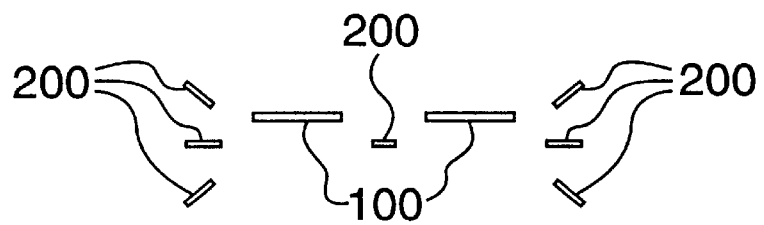
FIGS. 3(a)–(d) are various representations of the visual cue display as it reflects the true position of the user with respect to his environment.
Figure 3B:
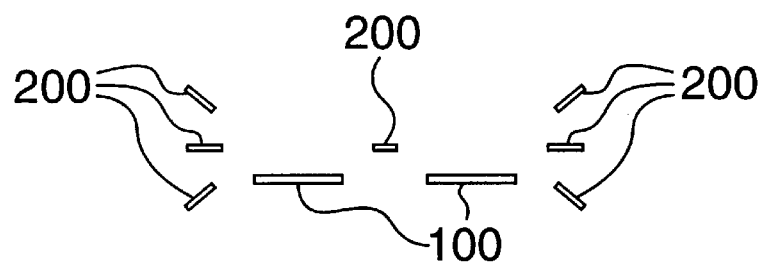
Figure 3C:
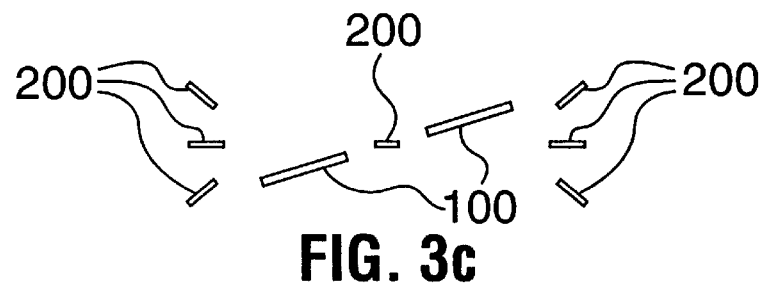
Figure 3D:
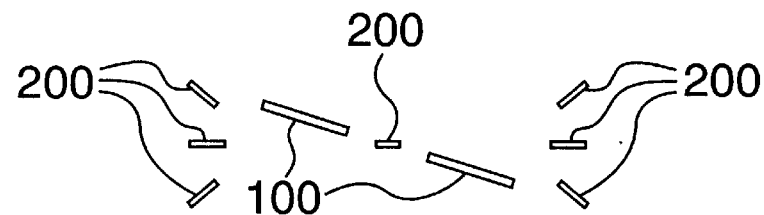

Turning now to FIG. 2, orientation markings (100 and 200) are shown as a stylized representation of one possible display perceived by the user of the instant invention. Moveable visual cue marks (100) are displayed in relation to a field of fixed orientation marks (200). Moveable visual cue marks (100) will change their position with respect to fixed orientation marks (200) whenever the position of frame (45) changes with respect to the true horizon. If orientation sensors (10) are mounted to a frame (45), which is in turn affixed to the user's head, the display presented to the user will correspond roughly to that shown in FIG. 2 when the user's head is positioned so as to be straight and level. Turning now to FIG. 3, it can be seen how the position of moveable visual cue marks (100) will change with respect to fixed orientation marks (200) as the user's head position changes. FIGS. 3(a)–(d) show how the display changes when the user's head moves up, down, left, and right, respectively. Such changes assume that all orientation sensors are affixed to the user's head (e.g., by using glasses frame (40)).

The changing orientation display gives the user visual cues as to the difference between his head position and that of his environment. Thus, users experiencing nausea and/or vertigo because they lack knowledge as to their physical position within the environment now have access to a simple means of determining their true relative orientation.

FIG. 4 illustrates several additional examples of visual cues which can occur in the present invention. It should be noted that such visual cues are by no means limited to those shown in the accompanying figures. That is, instead of various combinations of dashed or dotted lines, and the geometric shapes shown, other forms of visual cuing are contemplated. For example, the intensity or color of the display can be varied over its entire surface, or in specified areas, to indicate various conditions of orientation. Colors may be bright or muted, intensities may also be brightened or dimmed, and geometric figures or indicators can change shape, color, or intensity to indicate various orientations to a specific user. In addition, display visual cues can be tailored to each individual user, so that the user need only adapt to those visual cues he needs to properly navigate in his own environment and avoid the disabling affects of vertigo and motion sickness.

Figure 4A:
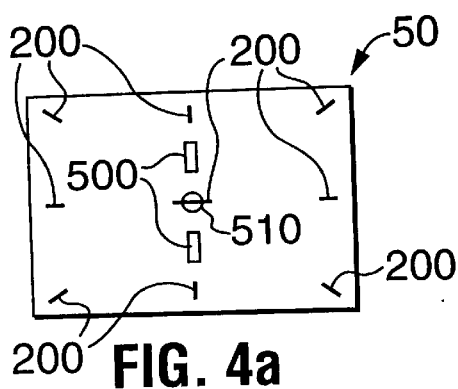
FIGS. 4(a)–(h) are alternative representations of the visual cue display as it reflects the position of the user with respect to his environment.
Figure 4E:
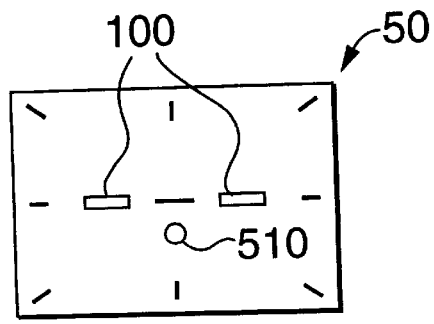
Figure 4B:
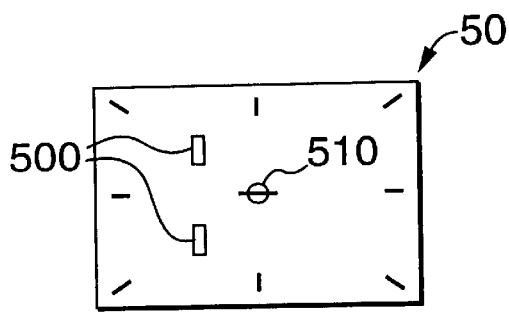
Figure 4F:
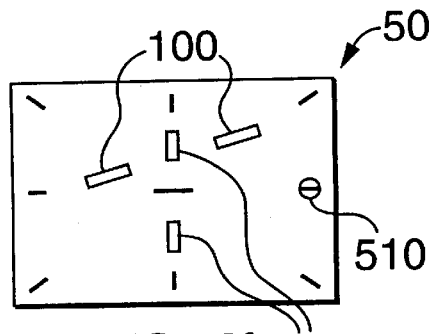
Figure 4C:
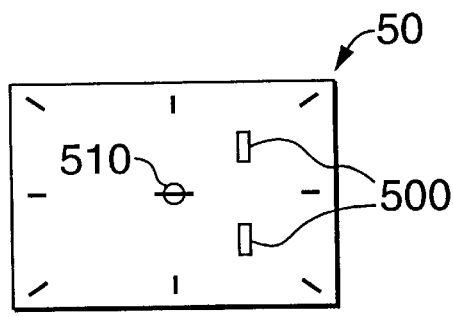
Figure 4G:
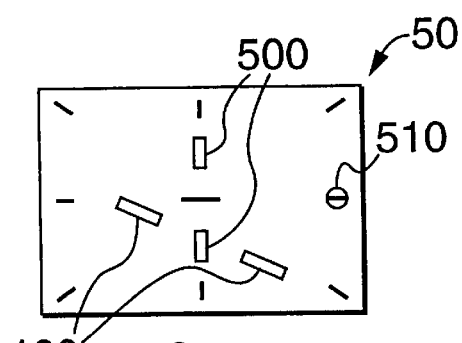
Figure 4D:
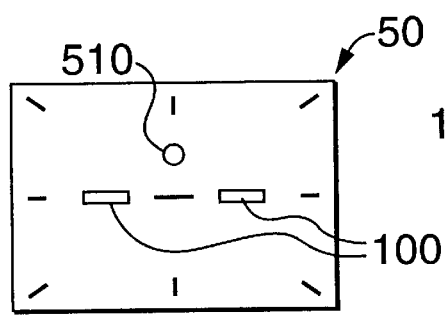
Figure 4H:
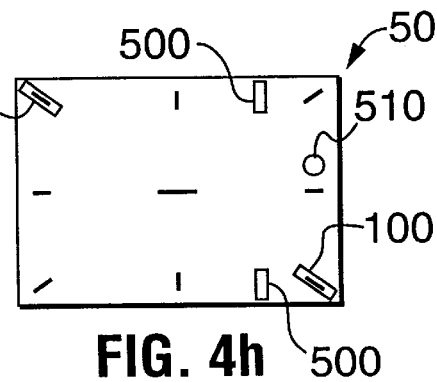

FIG. 4(a) represents a display providing two additional elements contemplated by the present invention. Vertical yaw bars (500) are used to indicate rotational position changes about an axis which extends from the head to the toes of the user. Elevational bubble (510) is used to indicate changes in altitude of the user's body from an initial baseline position. As can be seen in FIG. 4(b), the user has rotated toward his left about the central axis of his body. In FIG. 4(c), the user has rotated toward his right. In FIG. 4(d), the user has been elevated to some distance above an initial baseline rest position, and in FIG. 4(e), the user has been moved to a lower elevation than he initially encountered at the baseline rest position.

The present invention also anticipates a combination of visual cues from any number of orientation sensors, all operating at the same time. That is, a particular user may require roll (rotational movement about an axis which extends from the front to the back of the user), pitch (rotation about an axis which extends from the left to the right of the user), yaw (rotational movement which occurs about an axis which extends from the head to the toes of the user), and elevation (change in altitude above or below a baseline rest position) change information simultaneously. FIG. 4(f) illustrates such a combination of visual cues. In this case, the user has pitched backward and rolled to the left. Altitude and yaw remain unchanged. Note that elevation bubble (510) is now located at the side of the display. The present invention contemplates location of various visual cues at any place on the display which is convenient to the user, and most effective at transmission of orientation information to the brain for processing. FIG. 4(g) indicates that the user has pitched forward and rolled to the right. Elevation and yaw remain unchanged. Finally, FIG. 4(h) indicates that the user has rolled to the right, yawed to the right, and been elevated upwardly. Pitch has not changed. All orientation marks in FIG. 4(h) (both moving and stationary) have been relegated to the periphery (75) of the display (50). This allows use of the display for unobstructed views of objects in front of the user, while still providing needed visual orientation cues.

Figure 5:
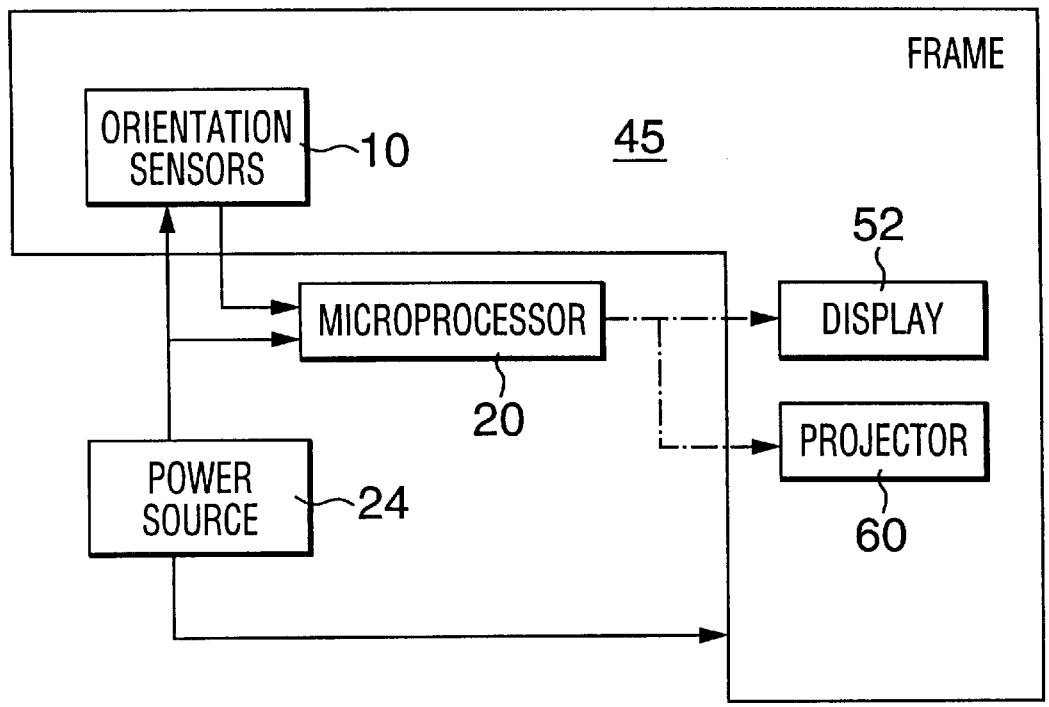
FIG. 5 is a simplified block diagram of an alternative embodiment of the invention.

Turning now to FIG. 5, a simplified block diagram of the preferred embodiment of the present invention can be seen. Frame (45) may consist of glasses frame (40), as shown in FIG. 1, or any other convenient means to mount the required components of the present invention, so as to make them easily transportable by the user. Orientation sensors (10) are preferably mounted to frame (45). Orientation sensors (10) can be any type among several commonly available, including gyroscopic, accelerometer, or magnetostrictive. Orientation sensors (10) are energized by power source (30), which can be batteries or some other portable mechanism (e.g., solar). Power source (30) also supplies power to microprocessor (20) and other elements, such as a display (50) or projector (60), which are also preferably mounted to frame (45). The output of orientation sensors (10) is sent to microprocessor (20) and translated by means of a program into display commands for display (50) or projector (60) mounted on frame (45). If display (50) is used, it must be transparent so as to interpose only the orientation markings (100 and 200) as shown on lenses (90) in FIG. I between the eyes of the user and his environment. The display (50) mechanism can be affixed to corrective lenses or incorporated into clear glass or other transparent material for use with frame (45).

An alternative means of presenting orientation markings (100 and 200) for perception by the user is to make use of a projector (60) to replace the function of display (50). Projector (60) is preferably mounted onto frame (45) in such a way as to project out into space in front of the user, by laser beam holographic means or other means, a display similar to that shown in FIG. 1, to include orientation markings (100 and 200). Commands to projector (60) are derived from signals produced by microprocessor (20) in response to input provided by orientation sensors (10). The projected display should preferably appear to be located several feet in front of the user.

Figure 6:
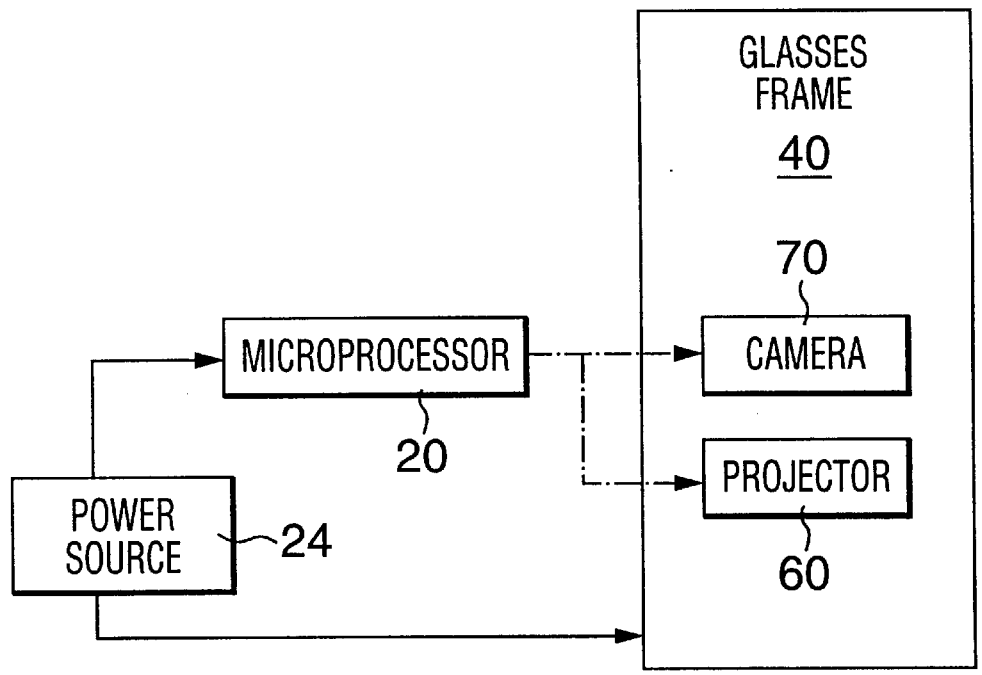
FIG. 6 is a simplified block diagram of an alternative embodiment of the present invention.

An alternative embodiment of the invention is shown in FIG. 6. In this case, no visual cue marks are displayed. The means to give the user visual clues as to orientation is now effected by producing an averaged semi-real-time display of what normally would be viewed through the lenses (90) of glasses frame (40) (of FIG. 1). In this case, a microprocessor (20) is powered by power source (30) which also provides power to a camera (70) (or series of cameras) and a projector (60). Camera (70) and projector (60) are preferably both mounted on glasses frame (40). In this embodiment of the instant invention, camera (70) can be used to produce a recorded image of the scene in front of the user. The recorded image is sent to microprocessor (20) and averaged with other images produced by camera (70) so as to produce what is perceived by the user to be a slowly changing display of the visual environment. This changing display is projected onto lenses (90) for actual perception by the user via projector (60). Thus, the user does not perceive the actual scene as recorded by camera (70), but only the averaged image as displayed by projector (60) on the inner surface of lenses (90).

Figure 7:
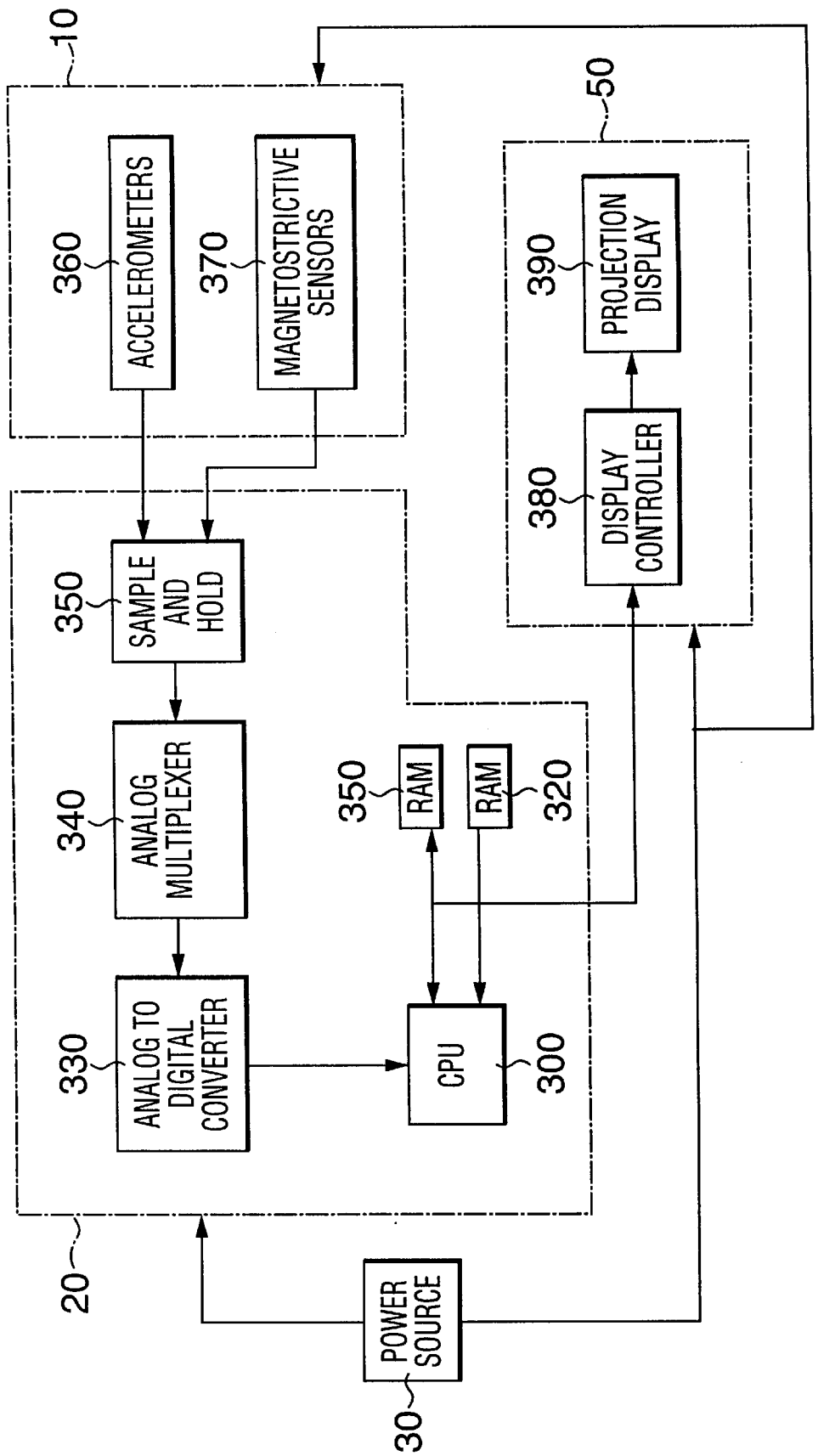
FIG. 7 is a block diagram of an alternative embodiment of the present invention, realized as an operational system.

Turning now to FIG. 7, an operational realization of the preferred embodiment using conventional components can be seen. Power source (30) is used to supply microprocessor (20) and, indirectly, display (50) and orientation sensors (10). Microprocessor (20) is composed of a personal computer central processor unit (300) or equivalent, connected to conventional random access memory(310), and non-volatile memory (320).

Projection display (390) is directly connected to display controller (380), which in turn is interfaced to a serial port on the central processor (300). A program is resident in the non-volatile memory (320), and used to direct the display controller (380), so as to project a series of visual cues onto projection display (390). Random access memory (310) is used as a scratchpad memory to store sensor input information and make calculations to update the visual cues sent to projection display (390) via display controller (380). The combination of analog-to-digital converter (330), analog multiplexer (340), and sample-and-hold (350) are integrated into a single circuit card made by Crossbow (Part No. CXLDK RS232, digital interface card), or equivalent. Orientation sensors (10) may take the form of a triaxial accelerometer(360), also made by Crossbow (Part No. CXL04M3) and three magnetostrictive sensors (Honeywell Part No. HMC1001).

Figure 8:
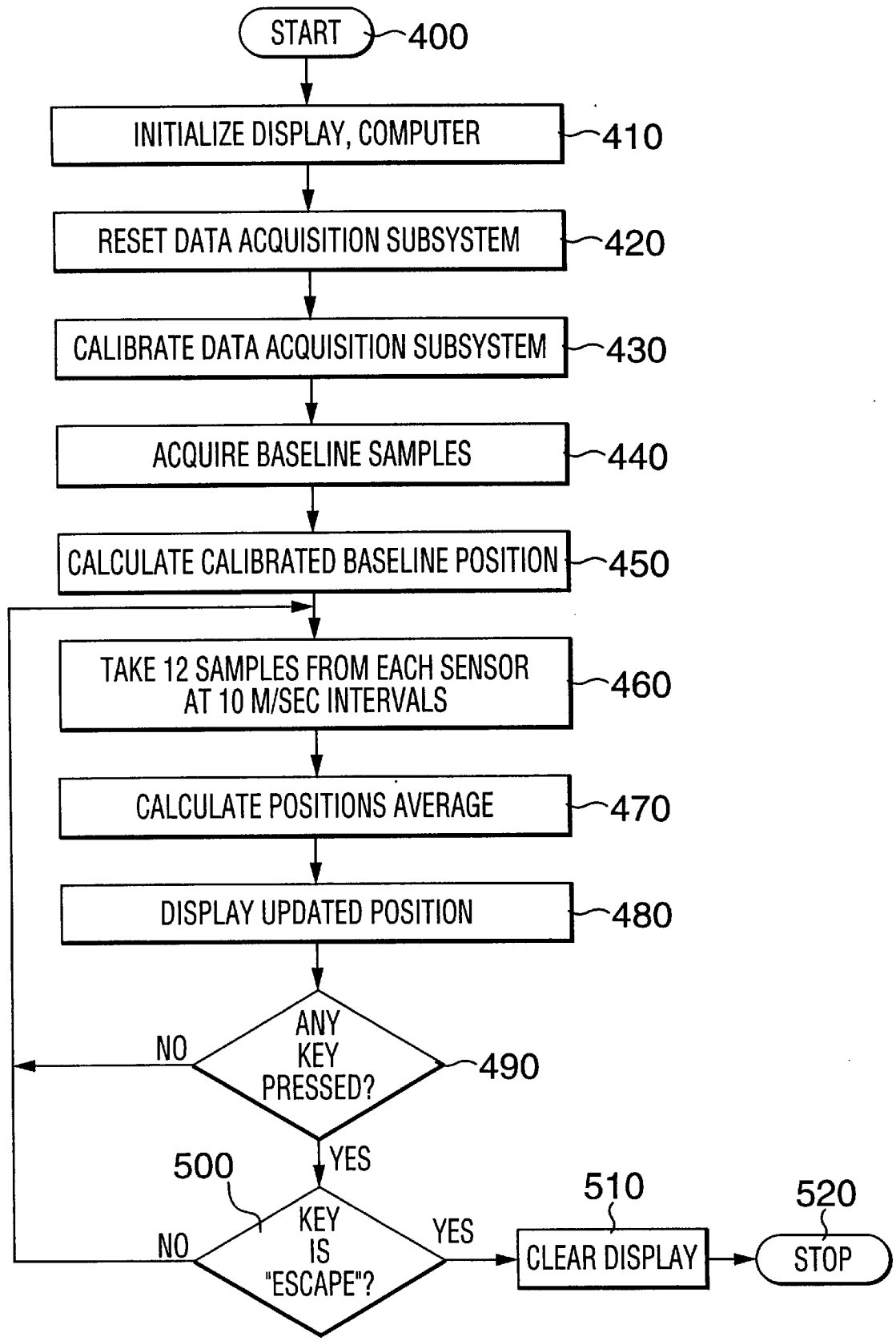
FIG. 8 is a summary flow chart illustration of the processing steps for implementing the method of the present invention.

Turning now to FIG. 8, a summary flow chart sequence of events necessary to effect the method of the present invention, given the specific implementation as shown in FIG. 7, can be seen. In step (400), the system is powered-up and microprocessor (300) is used to initialize display control (380) and scratch pad random access memory (310). In addition, the data acquisition sub-system consisting of analog-to-digital converter (330), analog multiplexer (340), and the sample-and-hold (350) are reset and prepared to accept data from accelerometer sensors (360) and magnetic sensors (370) in step (420).

Accelerometer sensors (360) are responsive to the Earth's gravitational field, which is relatively constant in magnitude and direction. The amount of angular tilt or acceleration experienced by each of accelerometer sensors (360) is passed on to sample-and-hold (350) in the form of a voltage, which is proportional to the change between the baseline (i.e. rest) position, and any newly measured position. Likewise, magnetic sensors (370) are responsive to changes in the Earth's magnetic field. Given a constant current input, the resistance of magnetic sensors (370) will change in proportion to changes in magnetic field strength. Thus, magnetic sensors (370) also provide a voltage indicative of positional change (from a baseline) to sample-and-hold (350).

To obtain a baseline (resting or initial reference)position measurement, accelerometer sensors (360) and magnetic sensors (370) are placed on a stable, non-moving surface, and the data acquisition sub-system consisting of analog-to-digital convertor (330), analog multiplexer (340), and the sample-and-hold (350) are calibrated by subjecting the system to test voltage inputs over a specific range (e.g. 0.0 to 5.0 volts), and obtaining a range of expected conversion values (i.e. conversion slope) in step (430). In step (440), the system is programmed to take about 100 samples from each sensor. These samples are averaged for each sensor, and recorded as the initial baseline (i.e. "at rest") position in step (450).

Now the microprocessor (300) enters a program loop which begins at step (460) and requires taking orientation sensors (10) data every 10 msec to produce a data set consisting of 12 samples of each sensor (e.g., 4 sensors×12 samples=48 samples in the set, if orientation sensors (10) consist of a triaxial accelerometer and a single magnetostrictive sensor), every 120 msec. In step (470), microprocessor (300) calculates the average position derived from the sample data for each sensor.

Finally, in step (480), the average measured position for each sensor is compared to the baseline position and the new, updated position sensed by the orientation sensors (10) is presented to the user via projection display (390) after the appropriate commands have been sent to display controller (380).

In this particular implementation of the preferred embodiment, the microprocessor (300) will look to see if any key on the computer keyboard (not shown) has been pressed in step (490). If it has, then the microprocessor (300) will exit from the data acquisition and positional update loop if the key pressed was an "ESCAPE" in step (500). If the key pressed was not an "ESCAPE", then microprocessor (300) will loop to step (460) and begin to acquire a new multi-sample data set based on any changes in orientation as sensed by accelerometer sensors (360) and magnetostrictive sensors (370).

If the microprocessor (300) has sensed an "ESCAPE" key input in step (500), then projection display (390) is cleared of all visual cues and the system is prevented from acquiring any more position-dependent data or displaying changes in that data in step (520), and the program is halted.

Figure 9:
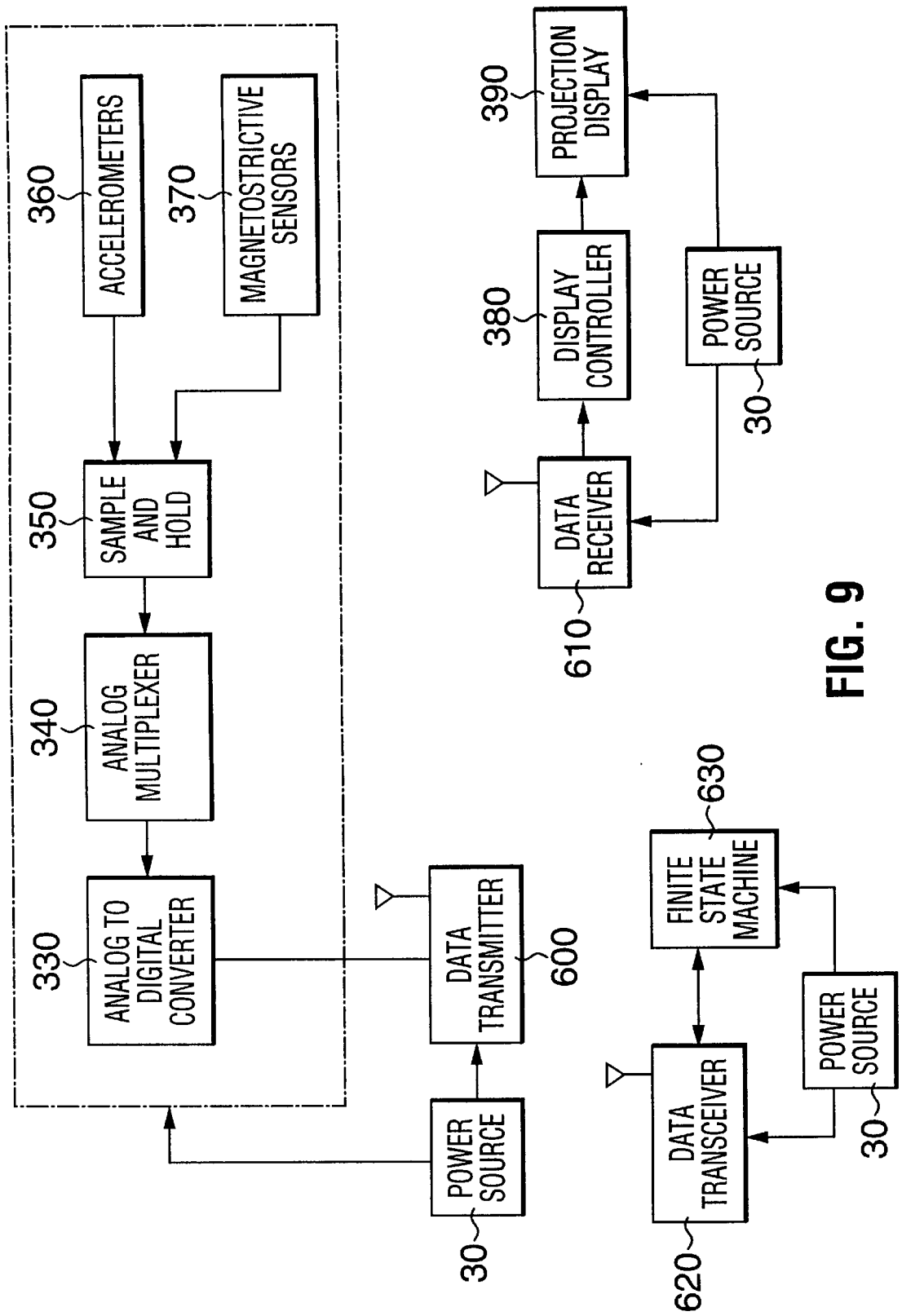
FIG. 9 is a block diagram of an alternative embodiment of the present invention.

The spirit of the present invention anticipates the partition of the data acquisition, data processing, and visual cue display functions of the system into separate units, or combined into a single monolithic unit. Implementation as separate units can be seen in FIG. 7, although other methods of partition are possible. For example, the data acquisition and display functions can be combined into a single head-mounted unit, and the data processing system can be remotely located to reduce weight and/or power requirements. In FIG. 9, the data acquisition function of the present invention is implemented by using a power source (30) to supply the data acquisition sub-system (consisting of analog-to-digital convertor (330), analog multiplexer (340), and the sample-and-hold (350)), data transmitter (600), and various orientation sensors (10), consisting of accelerometer sensors (360) and magnetostrictive sensors (370). In this system, positional input data is provided by the orientation sensors (10), acquired by the data acquisition sub-system, and provided to the data transmitter (600) for transmission to the data processing sub-system.

The data processing sub-system consists of a data transceiver (620) which sends the acquired data from orientation sensors (10) to a finite state machine (630) for processing. A power source (30) is also required at this juncture to energize data transceiver (620) and finite state machine (630). After processing of the positional sample data is completed, finite state machine (630) sends the resulting display controller information, along with any other data which may be desired (e.g., GPS, altitude, etc.), to the data transceiver (620). At this point, all data is received by data receiver (610) and passed on to display controller (380) for presentation to the user at projection display (390). Again, a power source (30) is used to supply the requirements of the data receiver (610), display controller (380), and projection display (390). It should be noted that all data communications which occur between data transmitter (600), data receiver (610), and data transceiver (620) can be effected by either radio frequency means, infrared means, or other wireless methods of communication.

Figure 10:
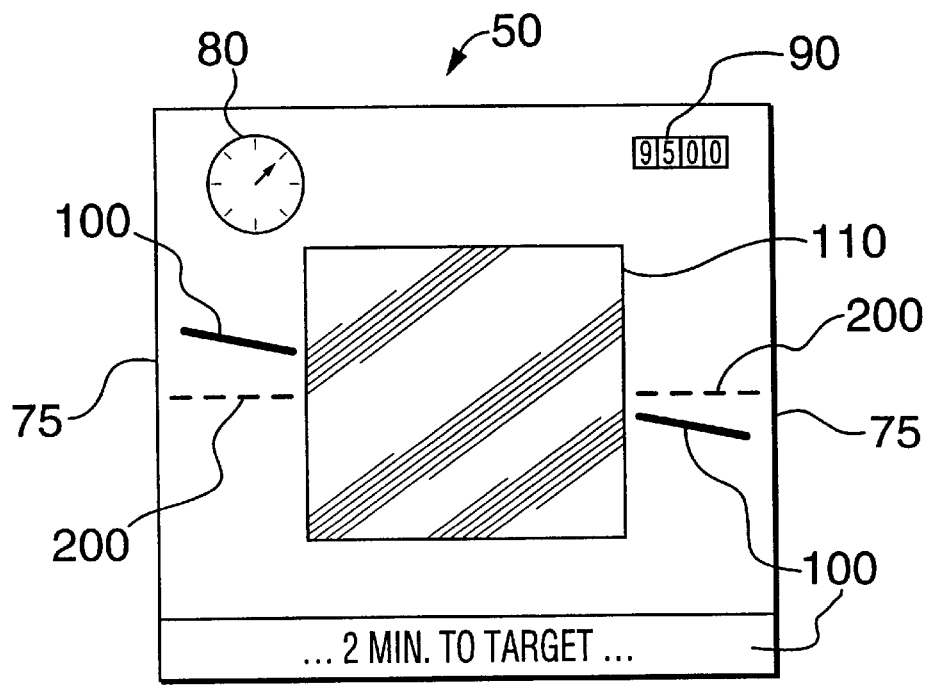
FIG. 10 is a stylized representation of the visual cue display with user messaging capability.
Figure 11:
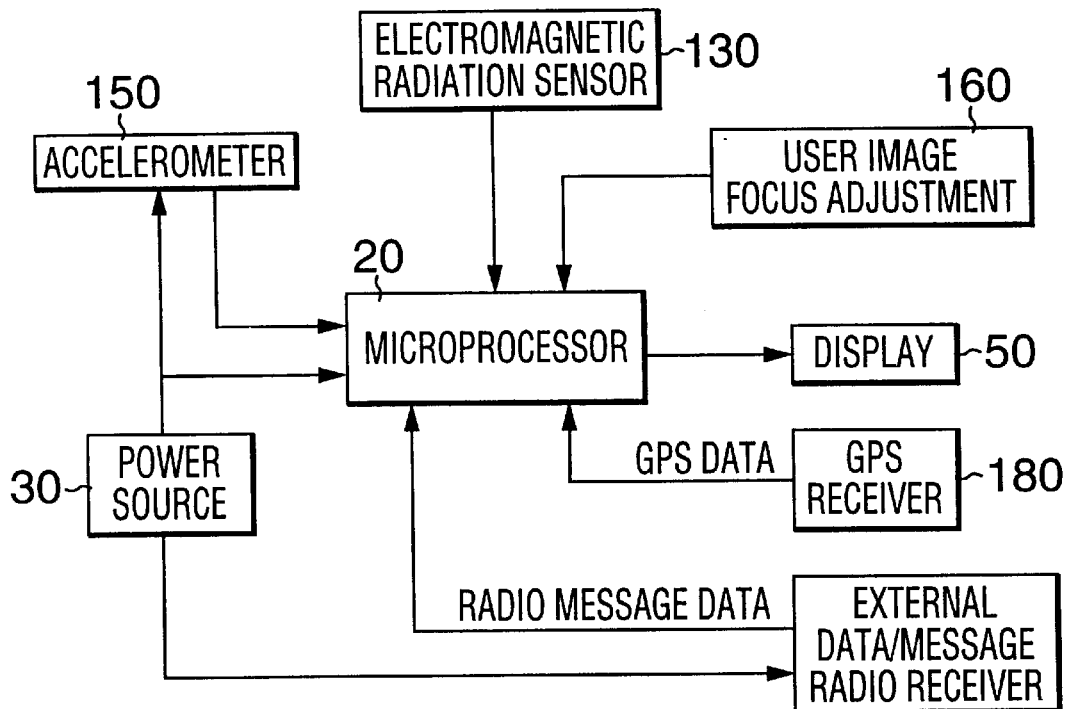
FIG. 11 is a simplified block diagram of an alternative embodiment of the present invention.
Figure 12:
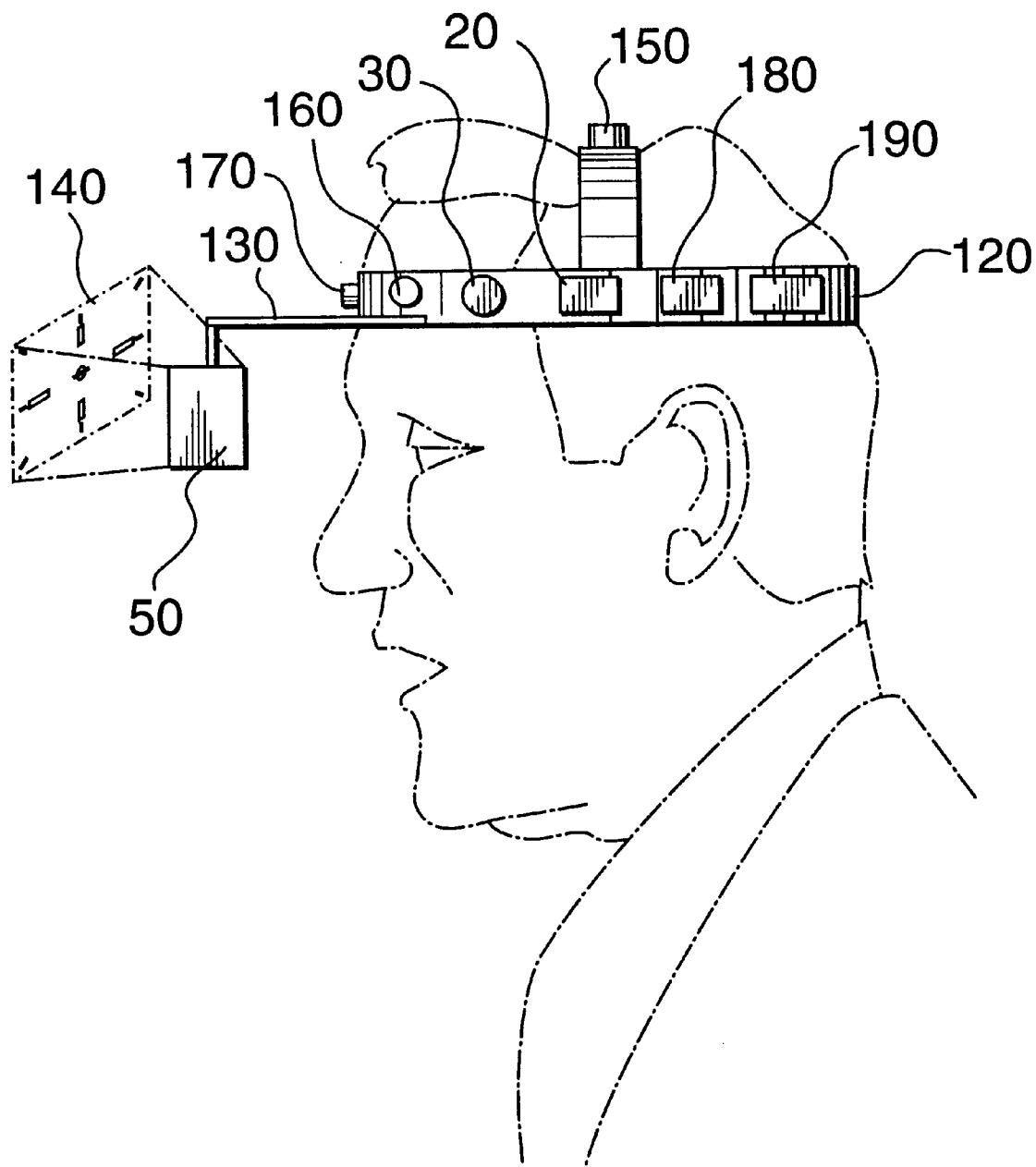
FIG. 12 is a perspective view of an alternative embodiment of the present invention indicating a user's perception of a projected visual cue image.

Many other possible implementations will suggest themselves to those skilled in the art. For example, this invention may be used in either civilian or military applications. Referring now to FIGS. 10, 11, and 12, an enhanced version of the invention can be seen. In this case, orientation information is projected out into space, several feet in front of the wearer, and provided at the periphery of the wearer's vision area (75). A miniaturized radio data receiver (e.g., cellular phone with modem, or similar device) (190) can be added to the basic system shown in FIG. 2, so that microprocessor (20) may also receive data which is unrelated to the user's position within his environment (See FIG. 10). Circuitry similar to that used in modern cordless or cellular phones, or digital messaging pagers, can also be used to directly interface with the microprocessor for wireless data transfer (20). In a military application, such information as target speed (80) and altitude (90) can be displayed at the top of the wearer's vision area display, and real-time messages which give an indication to the wearer of target proximity could be displayed in a "movie marquee" fashion at the bottom of the display (100). The center of the display (110) can be left open, as shown in FIG. 10, for display of any type of information which can be received over the radio/data link. The use of such display messaging in the military version of this invention obviates the need for verbal communications in many circumstances. This can be a real advantage in the battlefield or other situations where verbal or sonic communication is undesirable. The visual cue orientation display may also be superimposed onto a virtual reality display field (e.g. video games, flight simulators, etc.) or presented in conjunction with night-vision display applications. In naval or marine applications, the entire system worn by the user may have to be constructed in a water resistant or waterproof fashion. In this case, the central display area (110) might be used to display fleet position information (mapping) to the wearer.

It is not necessary in all circumstances to provide visual cue information to each eye of the wearer. In low cost civilian applications, for example, only a single display element may be required. See FIG. 12. Various methods of mounting the display are possible. For example, a band (120) can be used to mount the unit on the head of the wearer with a simple extendable arm (130) to place the display (50) in front of the wearer's eye (e.g., similar to the inspection mirror worn by doctors, or some jeweler's loupes). Physically, display (50) is preferably about one square inch in size. However, the user will actually perceive a display image (140) which is much larger, and projected out into the space in front of him. The invention for civilian use should be very light weight, inexpensive and rugged. If a radio data receiver is used with the visual cue display, such information as news, weather updates, or other information of interest can be displayed in an updated fashion on the peripheral edges of the display.

Turning now to FIGS. 11 and 12, it can be seen that other embodiments of the invention may include a three-axis accelerometer (150) in place of the orientation sensors (10) shown in FIG. 2. Of course, three separate single-axis accelerometers can also be used to replace orientation sensors (10). The use of accelerometers in place of a gyroscope will allow cost savings in some instances, and increase the ruggedness of the device.

In more sophisticated versions of this device, the display can be adjusted by the wearer to compensate for vision deficiency (i.e., diopter adjustment, similar to that used in binoculars) so that the projected information display appears to be in perfect focus at a distance from the user. This adjustment can be programmed into the microprocessor (20) by sensing a user-controlled input (160), or mechanically adjusted by moving the display (50) closer to or farther away from the user's eye.

Display (50) can be manufactured so that it is capable of displaying different elements in color. This will allow the wearer to immediately differentiate background information from priority or emergency information (e.g., emergency information can be displayed in red, while all other information is displayed in black and/or yellow). Display (50) can also be manufactured with a filter component to protect the eye of the wearer from damage by intense sources of electromagnetic energy. This may include simple polarizing filters or some type of material whose optical transmission properties can be adjusted to protect the eyesight of the wearer, depending on the optical sensing properties of the display material, or of an additional electromagnetic sensor (170) connected to microprocessor (20). Finally, retinal scanning, such as that described in "A Retinal Display for Virtual Environment Applications" (Proceedings of Society for Information display, 1993 International Symposium, Digest of Technical Papers, Vol. XXIV, pg. 827) or holographic projection, can be used to present appropriate visual cues to the user, with additional communications or message data if desired. Such technology would obviate the need for fixed display means for providing visual cues to the user.

An alternative embodiment of the present invention may also include GPS (global positioning satellite) information processing capability. That is, messaging display (50) can present location information to the user, or a map display which is automatically updated as the user moves along terrain. GPS information processing capability is also useful to underwater divers. In this case, the diver's underwater position updates could be displayed in real-time as GPS receiver (180) obtains locational updates from satellites overhead and ports the resulting data to microprocessor (20).

In order for the implementation of the present invention to be effective, it is important that the visual cue display information be processed and analyzed in a timely manner. This means that the display update for orientation visual cues (i.e. "physical sensation" information) should not lead or lag visual verification by a time period of greater than 150 msec, which means that orientation sensors (10) must normally be mounted on the head of the user. Head mounting of orientation sensors (10) will speed up the acquisition of any movement sensation resulting from changes in user physical position. If the orientation sensors (10) are mounted at some other location, it may be more convenient for the user, but may not be as effective at elimination of sensory mismatch as would direct mounting to the user's head. However, there may be instances in which the user desires to monitor the motion of an object moving with his own body, in which case the orientation sensors (10) must be mounted directly to that object, such as a car or airplane in which the user travels. In the described implementation of the embodiment depicted by FIG. 7, it was determined that a sensor sampling period of 120 msec, coupled with calculation of position change and display update commands of less than 30 msec, was sufficient to eliminate sensory mismatch (i.e. the display was continuously updated with new positional change information every 150 msec, or less). By supplying the user's brain with true conditions of motion within the required time period, sensory mismatch is eliminated and the user is relieved of vertigo and/or nausea that may result. This invention is also useful to those who have undergone the procedure of vestibular nerve section. Usually it takes months of rehabilitation to overcome the effects of such a procedure, but with the use of the present invention it is believed that rehabilitation can occur much more rapidly and successfully. Use of the artificial labyrinth will also lead to reductions in rehabilitation cost, since patients can get back to work more quickly, and drugs used to relieve the symptoms of sensory mismatch are avoided.

Although the invention has been described with reference to a specific embodiment, this description is not meant to be construed in a limiting sense. On the contrary, even though only specific devices have been shown to be mounted to the glasses frames, all elements of the instant invention can be mounted on these frames, given sufficient miniaturization. Also, various alternative stylized displays can be used, other than that shown in FIG. 3. As long as the user is given visual orientation cues which reflect motion such as pitch, roll, yaw, or elevation of his body with respect to the environment, the spirit of this invention is effected. This includes the use of mechanical orientation sensing devices placed within the user's normal viewing field to give appropriate visual cues. Other various modifications of the enclosed embodiments will become apparent to those skilled in the art upon reference to the description of the invention. It is, therefore, contemplated that the following claims will cover such modifications, alternatives, and equivalents that fall within the true spirit of the scope of the invention.

I claim:

1. A system for providing visual orientation information to a user, comprising:

orientation sensing means for providing positional change information of said user with respect to a baseline position of said user;

data acquisition means to acquire said positional change information of said user and said baseline position of said user from said orientation sensing means;

data processing means for determination of a relative positional change of said user from said baseline position of said user, based upon said positional change information of said user and said baseline position of said user acquired by said data acquisition means; and display means for presenting to said user a set of visual cues indicative of said relative positional change of said user.

2. The system of claim 1 wherein said orientation sensing means comprises an accelerometer.

3. The system of claim 1 wherein said orientation sensing means comprises a magnetostrictive sensor.

4. The system of claim 1 wherein said orientation sensing means comprises a gyroscope.

5. The system of claim 1 wherein said orientation sensing means is worn by said user on a band affixed to the head of said user.

6. The system of claim 1 wherein said display means is affixed to a pair of eye glasses.

7. The system of claim 1 wherein said display means comprises a liquid crystal display.

8. The system of claim 1 wherein said display means comprises a retinal scanner.

9. The system of claim 1 wherein said display means comprises the projection of a series of averaged video images acquired by a camera.

10. The system of claim 1 wherein said display means comprises a holographic projection.

11. The system of claim 1 wherein said visual cues comprise relative pitch orientation information.

12. The system of claim 1 wherein said visual cues comprises roll orientation information.

13. The system of claim 1 wherein said visual cues comprise relative yaw orientation information.

14. The system of claim 1 wherein said visual cues comprise relative elevation orientation information.

15. A method of providing physical orientation information to a user comprising the following steps:

a. first sensing a baseline position of said user;

b. second sensing a positional change of sad user from said baseline position of said user;

c. computing a relative amount of said positional change of said user from said baseline position of said user; and d. presenting said relative amount of said positional change of said user as a series of visual cues to said user.

16. The system of claim 15 wherein said sensing steps comprise the use of an accelerometer.

17. The method of claim 15 wherein said sensing steps comprise the use of a magnetostrictive sensor.

18. The method of claim 15 wherein said sensing steps comprise the use of a gyroscope.

19. The method of claim 15 wherein said presenting step comprises providing non-orientation information to said user.

20. The method of claim 15 wherein said second sensing step comprises sensing a change in said user's pitch.

21. The method of claim 15 wherein said second sensing step comprises sensing a change in said user's roll.

22. The method of claim 15 wherein said second sensing step comprises sensing a change in said user's yaw.

23. The method of claim 15 wherein said second sensing step comprises sensing a change in said user's elevation.

24. The system of claim 15 wherein said presenting step comprises provision of a holographic image to said user.

25. The method of claim 15 wherein said presenting step comprises provision of a retinal scanning image to said user.

26. The method of claim 15 wherein said second sensing step is repeated a multiplicity of times, and wherein said computing step comprises the determination of an average of a set of positional change data acquired during the repetition of said second sensing steps.

27. The method of claim 26 wherein said repetition of said second sensing step occurs at a rate of more than 10 times per second.

28. The method of claim 15 wherein said presenting step occurs at a rate of more than 6 times per second.

29. The method of claim 15 further including the continuous repetition of steps b, c and d.

30. A system for providing visual orientation information to a user, comprising:

orientation sensing means for providing positional change information of an object moving with said user with respect to a baseline position of said user;

data acquisition means to acquire said positional change information of said object moving with said user and said baseline position of said user from said orientation sensing means;

data processing means for determination of a relative positional change of said object moving with said user from said baseline position of said user, based upon said positional change information of said object moving with said user and said baseline position of said user acquired by said data acquisition means; and display means for presenting to said user a set of visual cues indicative of said relative positional change of said object moving with user.

* * * * *

(12) EX PARTE REEXAMINATION CERTIFICATE (7816th)
United States Patent
Butnaru

(10) Number: US 5,966,680 C1
(45) Certificate Issued: Oct. 19, 2010

(54) MOTION SICKNESS/VERTIGO PREVENTION DEVICE AND METHOD

(75) Inventor: Hanan Butnaru, San Antonio, TX (US)

(73) Assignee: Wesley O. Krueger, San Antonio, TX (US)

Reexamination Request:
No. 90/007,713, Sep. 7, 2005

Reexamination Certificate for:
Patent No.: 5,966,680
Issued: Oct. 12, 1999
Appl. No.: 08/800,266
Filed: Feb. 13, 1997

Related U.S. Application Data

(60) Provisional application No. 60/017,753, filed on May 15, 1996, and provisional application No. 60/011,895, filed on Feb. 15, 1996.

(51) Int. Cl.
*A61M 21/00* (2006.01)
*G02B 27/01* (2006.01)

(52) U.S. Cl. .................................. 702/150
(58) Field of Classification Search .......... 345/8, 345/9; 340/979, 980; 349/11; 89/41.07
See application file for complete search history.

(56) References Cited

U.S. PATENT DOCUMENTS

| | | | | |
|---|---|---|---|---|
| 4,368,517 A | * | 1/1983 | Lovering | 701/16 |
| 5,051,735 A | | 9/1991 | Furukawa | 340/705 |
| 5,138,555 A | * | 8/1992 | Albrecht | 701/14 |
| 5,303,715 A | * | 4/1994 | Nashner et al. | 600/595 |
| 5,353,242 A | * | 10/1994 | Crosbie et al. | 703/8 |
| 5,388,990 A | * | 2/1995 | Beckman | 434/38 |
| 5,425,378 A | * | 6/1995 | Swezey et al. | 600/595 |
| 5,566,073 A | * | 10/1996 | Margolin | 701/213 |
| 5,585,813 A | * | 12/1996 | Howard | 345/8 |
| 5,613,022 A | | 3/1997 | Odhner et al. | 385/37 |
| 5,613,690 A | * | 3/1997 | McShane et al. | 273/449 |
| 5,629,848 A | * | 5/1997 | Repperger et al. | 701/14 |
| 5,645,077 A | * | 7/1997 | Foxlin | 600/587 |
| 5,717,392 A | * | 2/1998 | Eldridge | 340/996 |
| 5,727,098 A | | 3/1998 | Jacobson | 385/31 |
| 5,729,366 A | | 3/1998 | Yang | 359/13 |
| 5,745,054 A | | 4/1998 | Wilkens | 340/972 |
| 5,748,264 A | * | 5/1998 | Hegg | 348/746 |
| 5,790,085 A | * | 8/1998 | Hergesheimer | 345/8 |
| 5,807,284 A | * | 9/1998 | Foxlin | 600/595 |
| 6,064,398 A | * | 5/2000 | Ellenby et al. | 345/633 |
| 6,084,556 A | * | 7/2000 | Zwern | 345/8 |
| 6,160,666 A | * | 12/2000 | Rallison et al. | 359/630 |
| 6,317,103 B1 | * | 11/2001 | Furness et al. | 345/8 |
| 6,353,436 B1 | * | 3/2002 | Reichlen | 345/427 |
| 6,369,952 B1 | * | 4/2002 | Rallison et al. | 359/630 |
| 6,396,497 B1 | * | 5/2002 | Reichlen | 345/427 |

\* cited by examiner

*Primary Examiner*—Majid A. Banankhah

(57) ABSTRACT

A device and method which operates as an artificial labyrinth to eliminate sensory mismatch between the natural labyrinth/vestibular system and the vision system of an individual. The present invention provides an alternative means for the user to determine the true orientation of his body with respect to the surrounding environment. The method can be effected by means of a device which senses true body orientation and displays corresponding visual orientation cues that the brain can use to confirm other visual position information. The display can be projected into space in front of the user, directly onto the user's retina, or effected by pictorial scene averaging. The device is particularly useful in the rehabilitation treatment of persons suffering from vestibular nervous system defect or damage, and in providing relief to those suffering from the symptoms of nausea and/or vertigo which are often experienced as a result of the aforementioned sensory mismatch.

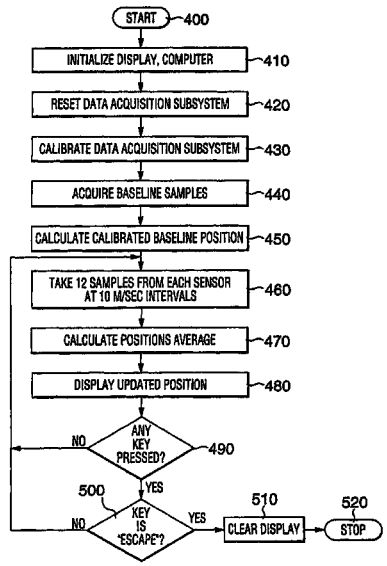

US 5,966,680 C1

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1, 15, 16, 24 and 30 are determined to be patentable as amended.

Claims 2–14, 17–23 and 25–29, dependent on an amended claim, are determined to be patentable.

New claims 31–84 are added and determined to be patentable.

1. A system for providing visual orientation information to a user, comprising:
   orientation sensing means for providing positional change information of said user with respect to a baseline position of said user;
   data acquisition means to acquire said positional change information of said user and said baseline position of said user from said orientation sensing means;
   data processing means for determination of a relative positional change of said user from said baseline position of said user, based upon said positional change information of said user and said baseline position of said user acquired by said data acquisition means; and
   display means for presenting to said user a set of visual cues indicative of said relative positional change of said user *which ameliorate the effects of sensory mismatch*.

15. A method of providing physical orientation information to a user *to ameliorate a sensory mismatch between the user's vestibular system and vision system* comprising the following steps:
   a. first sensing a baseline position of said user;
   b. second sensing a positional change of said user from said baseline position of said user;
   c. computing a relative amount of said positional change of said user from said baseline position of said user; [and]
   d. ameliorating a sensory mismatch between the user's vestibular system and vision system by presenting said relative amount of said positional change of said user as a series of visual cues to said user; *and*
   e. *ameliorating a sensory mismatch between the user's vestibular system and vision system*.

16. The [system] *method* of claim 15 wherein said sensing steps comprise the use of an accelerometer.

24. The [system] *method* of claim 15 wherein said presenting step comprises provision of a holographic image to said user.

30. A system for providing visual orientation information to a user, comprising:
   orientation sensing means for providing positional change information of an object moving with said user with respect to a baseline position of said user;
   data acquistion means to acquire said positional change information of said object moving with said user and said baseline position of said user from said orientation sensing means;
   data processing means for determination of a relative positional change of said object moving with said user from said baseline position of said user, based upon said positional change information of said object moving with said user and said baseline position of said user acquired by said data acquistion means; and
   display means for presenting to said user a set of visual cues indicative of said relative positional change of said object moving with user *which prevent or ameliorate the effects user sensory mismatch*.

31. *The method of claim 16 wherein said accelerometer comprises a triaxial accelerometer.*

32. *The method of claim 15 wherein said visual cues comprise cues relating to said user's yaw, pitch and roll.*

33. *The method of claim 15 wherein said presenting step comprises provision of a projected image.*

*The method of claim 15 wherein said presenting step comprises provision of an image projected directly onto said user's retina.*

35. *The method of claim 15 further comprising use of a night-vision display.*

36. *The method of claim 15 wherein said presenting step comprises provision of an image superimposed onto a virtual reality display field.*

37. *The method of claim 15 further comprising the step of receiving information from one or more global positioning satellites relating to said user's position.*

38. *The method of claim 15 further comprising the step of receiving information from one or more global positioning satellites relating to a vehicle's position wherein the user is traveling in said vehicle.*

39. *The methof of claim 37 further comprising presenting to said user visual cues pertaining to said user's position derived from the information from the one or more global positioning satellites.*

40. *The method of claim 38 further comprising presenting to said user visual cues pertaining to the vehicle's position derived from the information from the one or more global positioning satellites.*

41. *The method of claim 15 wherein said sensing steps comprise the use of one or more orientation sensing devices attached to a vehicle in which the user is traveling.*

42. *The method of claim 15 wherein said sensing steps comprise the use of one or more orientation sensing devices attached to the user or to an object worn by said user.*

43. *The method of claim 15 wherein said presenting step further comprises compensating for a vision deficiency of said user.*

44. *The method of claim 43 wherein said compensation comprises a diopter adjustment.*

45. *The method of claim 15 wherein said presenting step comprises providing visual cues integrated into glasses worn by the user.*

46. *The method of claim 15 wherein said visual cues comprise dashed or dotted lines.*

47. *The method of claim 15 wherein said presenting step comprises the presentation of visual cues that comprise colors of varying intensity.*

48. *The method of claim 15 wherein said presenting step comprises the presentation of visual cues that change shape, color, or intensity.*

49. *The method of claim 15 wherein said visual cues comprise yaw bars indicating said user's rotational position.*

50. *The method of claim 15 wherein said presenting step comprises providing fixed orientation marks and movable visual cue orientation marks.*

51. *The method of claim 15 wherein said presenting step comprises providing an averaged semi-real-time display.*

52. *The method of claim 15 wherein said presenting step comprises providing an averaged semi-real-time display.*

53. The method of claim 19 wherein said non-orientation information comprises textual information.

54. The method of claim 19 wherein said non-orientation information comprises graphical information.

55. The method of claim 15 wherein said orientation cues are superimposed onto a video game system.

56. A method of providing physical orientation information to a user aboard a dynamically moving vehicle comprising the following steps:
   a. first sensing a baseline position of said user aboard a moving vehicle about at least two axes;
   b. second sensing actual positional change of said user about at least said two axes from said baseline position of said user when the vehicle accelerates dynamically;
   c. computing a relative amount of said true positional change of said user from said baseline position of said user; and
   d. presenting said relative amount of said true positional change of said user about at least said two axes as a series of visual cues to said user whereby the effects of sensory mismatch between the users vestibular system and vision system are ameliorated or prevented.

57. The method of claim 56 where the vehicle is airplane.

58. A method of providing physical orientation information to a user comprising the following steps:
   a. first sensing a baseline position of said user about an axis;
   b. second sensing a positional change of said user from said baseline position of said user anywhere 360 degrees about said axis;
   c. computing a relative amount of said positional change of said user from said baseline position of said user; and
   d. presenting said relative amount of said positional change of said user as a series of visual cues to said user to ameliorate the effects of a mismatch of the user's vestibular system and vision system.

59. A method of providing physical orientation information to a user comprising the following steps:
   a. first sensing a baseline position of said user about at least two axes using sensors not dependent on gravity;
   b. second sensing a positional change of said user from said baseline position of said user;
   c. computing a relative amount of said positional change of said user from said baseline position of said user; and
   d. presenting said relative amount of said positional change of said user as a series of visual cues to said user to ameliorate the effects of a mismatch the user's vestibular system and vision system.

60. A method of providing physical orientation information to a user comprising the following steps:
   a. first sensing a baseline position of said user who is accelerating in one or more directions;
   b. second sensing a positional change of said user from said baseline position of said user;
   c. computing a relative amount of said true positional change of said user from said baseline position of said user; and
   d. presenting said relative amount of said true positional change of said user as a series of visual cues to said user whereby the effects of sensory mismatch between the users vestibular system and vision system are ameliorated or prevented.

61. A method of providing physical orientation information to a user comprising the following steps:
   a. first sensing a baseline position of said user with an accelerometer;
   b. second sensing a positional change of said user from said baseline position of said user with an accelerometer;
   c. computing a relative amount of said true positional change of said user from said baseline position of said user; and
   d. presenting said relative amount of said positional change of said user as a series of visual cues to said user to ameliorate the effects of a mismatch the user's vestibular system and vision system.

62. A method of providing physical orientation information to a user comprising the following steps:
   a. first sensing a baseline position of said user with a magnetostrictive sensor;
   b. second sensing a positional change of said user from said baseline position of said user with a magnetostrictive sensor;
   c. computing a relative amount of said positional change of said user from said baseline position of said user; and
   d. presenting said relative amount of said positional change of said user as a series of visual cues to said user to ameliorate the effects of a mismatch the user's vestibular system and vision system.

63. A method of providing physical orientation information to a user comprising the following steps:
   a. first sensing a baseline position of said user with a gyroscope;
   b. second sensing a positional change of said user from said baseline position of said user with a gyroscope;
   c. computing a relative amount of said positional change of said user from said baseline position of said user; and
   d. presenting said relative amount of said positional change of said user as a series of visual cues to said user to ameliorate the effects of a mismatch the user's vestibular system and vision system.

64. A method of providing physical orientation information to a user comprising the following steps:
   a. first sensing a baseline position of said user;
   b. second sensing a positional change of said user's role from said baseline position of said user;
   c. computing a relative amount of said true positional change of said user from said baseline position of said user; and
   d. presenting said relative amount of said true positional change of said user as a series of holographic visual cues to said user whereby the effects of sensory mismatch between the users vestibular system and vision system are ameliorated or prevented.

65. A method of providing physical orientation information to a user comprising the following steps:
   a. first sensing a baseline position of said user;
   b. second sensing a positional change of said user from said baseline position of said user;
   c. computing a relative amount of said true positional change of said user from said baseline position of said user; and
   d. presenting said relative amount of said true positional change of said user as a series of visual cues to said user to ameliorate the effects of a mismatch the user's vestibular system and vision system.

66. A method of providing physical orientation information to a user comprising the following steps:
   a. first sensing a baseline position of said user;
   b. second sensing a positional change of said user from said baseline of said user;
   c. computing a relative amount of said positional change of said user from said baseline position of said user; and
   d. presenting said relative amount of said positional change of said user as a series of visual cues to said user to ameliorate the effects of a mismatch the user's vestibular system and vision system.

67. A method of providing physical orientation information to a user comprising the following steps:
   a. first sensing a baseline position of said user;
   b. second sensing a positional change of said user from said baseline position of said user;
   c. computing a relative amount of said positional change of said user from said baseline position of said user; and
   d. presenting said relative amount of said positional change of said user as a series of retinal scanning image visual cues to said user to ameliorate the effects of a mismatch the user's vestibular system and vision system.

68. The method of claim 66 wherein said repetition of said second sensing step occurs at a rate of more than 10 times per second.

69. A method of providing physical orientation information to a user comprising the following steps:
   a. first sensing a baseline position of said user;
   b. second sensing a positional change of said user from said baseline position of said user;
   c. computing a relative amount of said true positional change of said user from said baseline position of said user; and
   d. presenting said relative amount of said true positional change of said user as a series of visual cues to said user updated at a rate of more than six (6) times per second whereby the effects of sensory mismatch between the users vestibular system and vision system are ameliorated or prevented.

70. A method of providing physical orientation information to a user comprising the following steps:
   a. sensing a baseline position of said user about a first axis;
   b. sensing a positional change of said user about said first axis from said baseline position of said user;
   c. sensing a baseline position of said user about a second axis;
   d. sensing a positional change of said user about said second axis;
   e. computing a relative amount of said true positional change of said user from said baseline position of said user about said first and second axes; and
   f. presenting together in one view said relative amount of said true positional changes of said user about said first and second axes as a series of visual cues to said user whereby the effects of sensory mismatch between the users vestibular system and vision system are ameliorated or prevented.

71. The method of claim 70 where the axes sensed are roll and pitch.

72. The method of claim 70 where the axes sensed are roll and yaw.

73. The method of claim 70 where the axes sensed are roll and elevation.

74. The method of claim 70 where the axes sensed are pitch and yaw.

75. The method of claim 70 where the axes sensed are pitch and elevation.

76. The method of claim 70 where the axes sensed are yaw and elevation.

77. The method of claim 70 which further includes sensing a positional change of said user about a third axis.

78. The method of claim 77 where the axes sensed are roll, pitch and yaw.

79. The method of claim 77 where the axes sensed are roll, pitch and elevation.

80. The method of claim 77 where the axes sensed are pitch, yaw and elevation.

81. The method of claim 77 where the axes sensed are roll, yaw and elevation.

82. The method of claim 70 which further includes sensing a positional change of said user about a third axis and fourth axis.

83. The method of claim 82 where the axes sensed are roll, pitch, yaw and elevation.

84. The method of claim 70 where the axes sensed are any two of roll, pitch, yaw and elevation.

\* \* \* \* \*